United States Patent [19]

Walker et al.

[11] 4,411,835

[45] Oct. 25, 1983

[54] PREPARATION OF CORTICOIDS FROM 17-KETO STEROIDS

[75] Inventors: Jerry A. Walker, Oshtemo Township, Kalamazoo County; Edward J. Hessler, Kalamazoo, both of Mich.

[73] Assignee: The Upjohn Company, Kalamazoo, Mich.

[21] Appl. No.: 378,939

[22] Filed: May 17, 1982

Related U.S. Application Data

[62] Division of Ser. No. 264,593, May 18, 1981, Pat. No. 4,357,279.

[51] Int. Cl.$^3$ .............................................. C07J 7/00
[52] U.S. Cl. .......................... 260/397.45; 260/239.5; 260/397.5

[58] Field of Search .................................. 260/397.45

[56] References Cited

U.S. PATENT DOCUMENTS 4,041,055  8/1977  Shephard et al. ............... 260/397.3
4,357,279  11/1982  Walker et al. .................. 260/397.45

OTHER PUBLICATIONS

J. Am. Chem. Soc. 86, 3840 (1964).
J. Org. Chem. 35, 2831 (1970).

*Primary Examiner*—Elbert L. Roberts
*Attorney, Agent, or Firm*—Bruce Stein

[57] ABSTRACT

The present invention is a process for the transformation of a 17-keto steroid (II) to a corticoid (XI) which has pharmaceutical utility.

18 Claims, No Drawings

PREPARATION OF CORTICOIDS FROM 17-KETO STEROIDS

This is a division of application Ser. No. 264,593 filed May 18, 1981 now U.S. Pat. No. 4,357,279.

The present invention relates to a process for preparation of pharmaceutically useful corticoids for which the essential material constituting a disclosure thereof is incorporated here by reference from divisional U.S. patent application Ser. No. 264,593, filed May 18, 1981, now U.S. Pat. No. 4,357,279.

I claim:

1. A process for the preparation of a corticoid of the formula

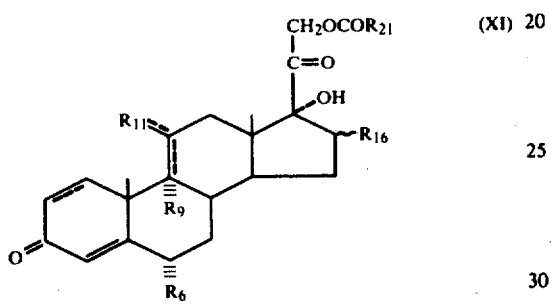

which comprises (1) contacting a protected 17-keto steroid selected from the group consisting of compounds of the formula

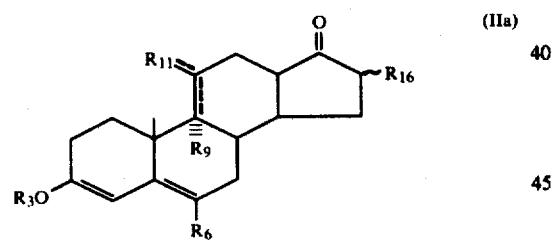

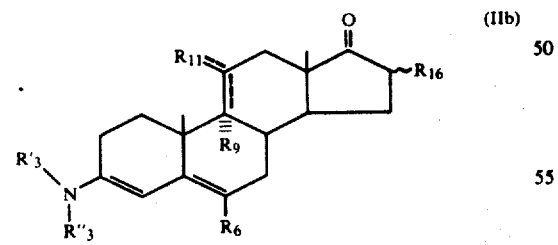

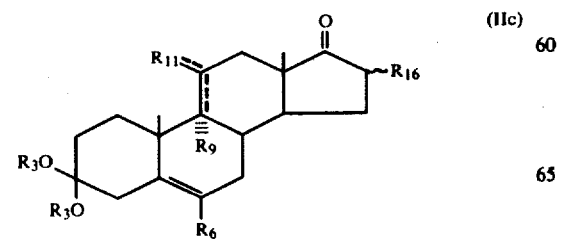

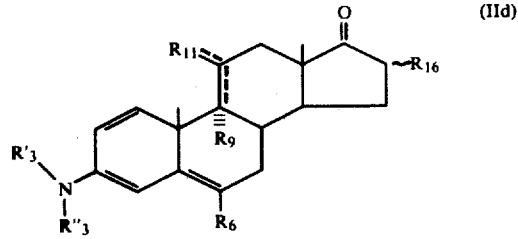

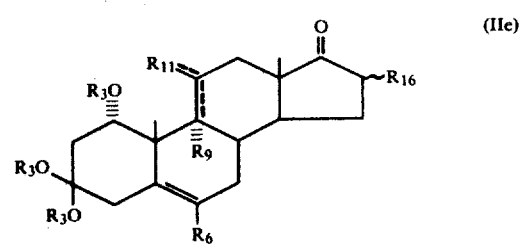

with a metallated 1,2-dihalogenated ethene of the formula

to form the corresponding protected $C_{21}$-steroid selected from the group consisting of compounds of the formula

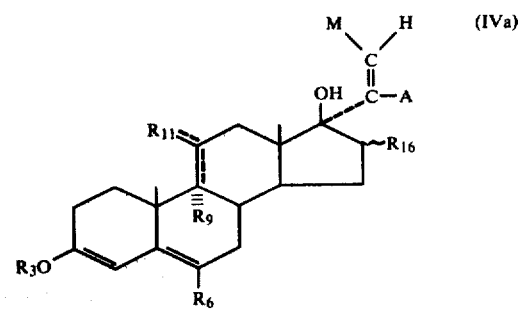

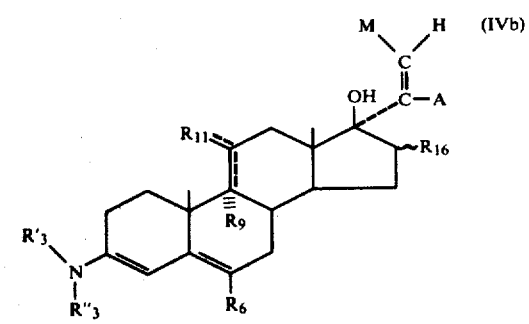

-continued

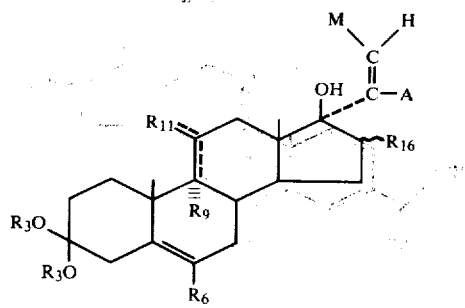
(IVc)

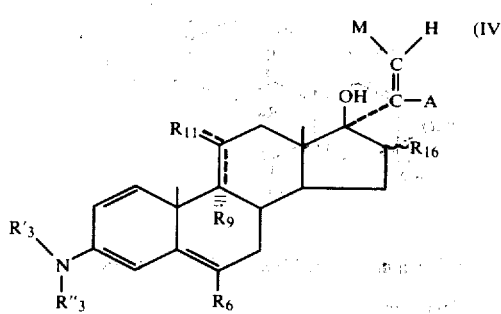
(IVd)

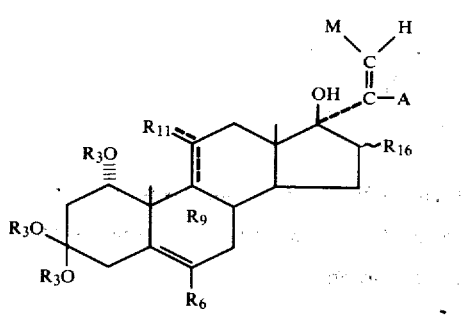
(IVe)

respectively;

(2) hydrolyzing the protected $C_{21}$-steroid (IVa–IVe) with acid to remove the protecting group and give a $C_{21}$-steroid of the formula

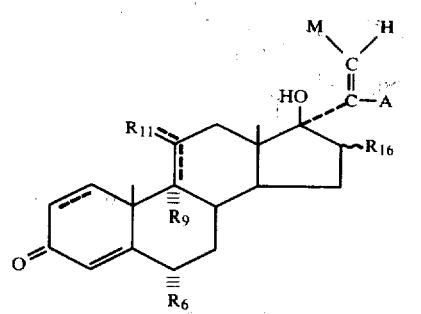
(V)

(3) contacting the $C_{21}$-steroid (V) with a sulfenylating agent of the formula

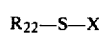
$R_{22}$—S—X (VI)

to give a 20,21-dihalo steroid of the formula

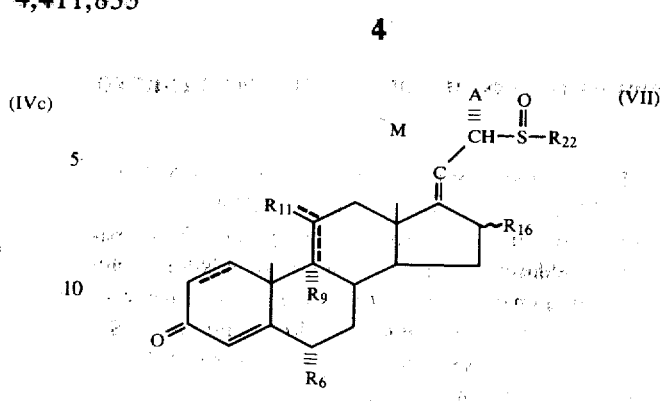
(VII)

(4) contacting the 20,21-dihalo steroid (VII) with a base selected from the group consisting of an alkoxide or mercaptide of the formula $OR_{20}^-$, or $SR_{20}^-$, respectively, to give a sulfoxide of the formula

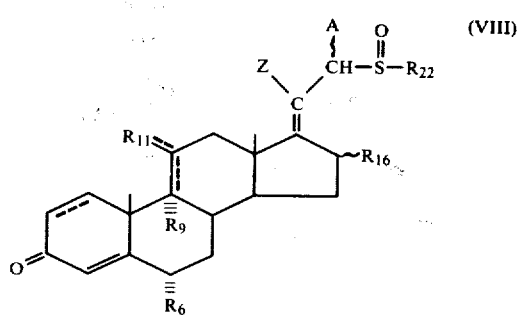
(VIII)

(5) contacting the sulfoxide (VIII) with a thiophile to give a 20-unsaturated steroid of the formula

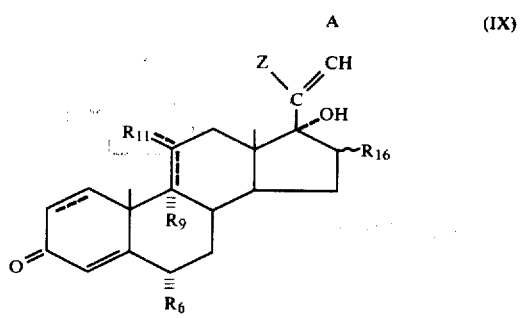
(IX)

(6) hydrolyzing the 20-unsaturated steroid (IX) with acid to give a 21-halo steroid of the formula

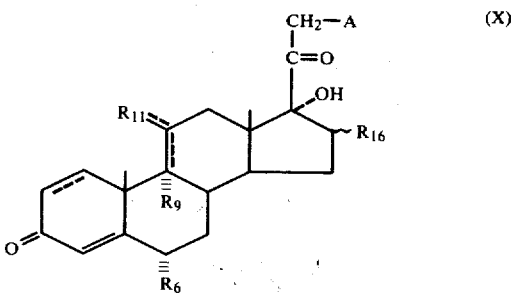
(X)

and (7) contacting the 21-halo steroid (X) with an anion of the formula $R_{21}CO^\ominus$ where A is a fluorine, chlorine or bromine atom; M is a fluorine, chlorine or bromine atom; $R_3$ is alkyl of 1 thru 5 carbon atoms with the proviso that with the ketal (IIIc and IIIe), the $R_3$ groups can be connected to form the ethylene ketal; $R_3'$ is alkyl of 1 thru 5 carbon atoms; $R_3''$ is alkyl of 1 thru 5 carbon atoms; $R_6$ is a hydrogen or fluorine atom or methyl group; $R_9$ is a hydrogen or fluorine atom, hydroxyl group, —OSi(R)$_3$ or nothing; $R_{11}$ is H, H,H, H, $\beta$-OH, H, $\beta$-OSi(R)$_3$, or O; $R_{16}$ is hydrogen atom or methyl group; $R_{20}$ is alkyl of 1 thru 4 carbon atoms or phenyl; $R_{21}$ is alkyl of 1 thru 4 carbon atoms or phenyl; $R_{22}$ is alkyl of 1 thru 5 carbon atoms, trichloromethyl, phenyl, phenyl substituted with 1-4 carbon atoms or substituted with 1 thru 3 nitro or trifluoromethyl groups, aralkyl of 7 thru 12 carbon atoms or —N—($R_{122}$)$_2$ or phthalimide; X is a chlorine or bromine atom, phenylsulfone, phthalimide or imidazole group; Z is —OR$_{20}$ or —SR$_{20}$; metal is lithium, sodium or potassium; $\infty$ indicates the attached group can be in either the $\bar{\alpha}$ or $\beta$ configuration; ···· is a single or double bond.

2. A process according to claim 1 where for the corticoid (XI), $R_6$ and $R_{16}$ are hydrogen atoms, where $R_9$ is nothing and $R_{11}$ is [H] which gives a $\Delta^{9,11}$ functionality in the C ring.

3. A process according to claim 1, where the temperature for the coupling reaction is from about $-120°$ to about $-20°$.

4. A process according to claim 1, where the coupling reaction is performed in a dry solvent.

5. A process according to claim 1, where the metallated 1,2-dihalogenated ethene (III) is selected from the group consisting of lithiated trans-1,2-dichloroethene, lithiated trans-1,2-chlorofluoroethene, lithiated trans-1,2-dibromoethene, lithiated trans1,2-difluoroethene and lithiated trans-1,2-bromofluoroethene.

6. A process according to claim 5 where the metallated 1,2-dihalogenated ethene (III) is lithiated trans-1,2-dichloroethene.

7. A process according to claim 1, where the acid to remove the $C_3$ protecting group is present in a catalytic amount.

8. A process according to claim 1, where the acid to remove the $C_3$ protecting group is selected from the group consisting of p-TSA, hydrochloric acid, sulfuric acid, and phosphoric acid.

9. A process according to claim 1 where for the sulfenylating agent. $R_{22}$-S-X, X is a chlorine or bromine atom, and $R_{22}$ is a phenyl group.

10. A process according to claim 1 where the temperature range for the sulfenylating reaction is from about $-80°$ to about $25°$.

11. A process according to claim 1, where the base is an alkoxide.

12. A process according to claim 11 where the alkoxide is methoxide or phenoxide.

13. A process according to claim 1, where the reaction with base is performed in a polar solvent.

14. A process according to claim 1, where 1.5–2.0 equivalents of base are used.

15. A process according to claim 1 where the thiophile is selected from the group consisting of acetone, 3-pentanone, cyclohexanone, 1-(phenylthio)acetone, 2,4-pentanedione, trimethylphosphite, mesityl oxide, dimethyl malonate, 2,6-di-t-butylphenol, ethylvinyl ether, and dihydropyran.

16. A process according to claim 1 where the thiophile is a ketone.

17. A process according to claim 16 where the ketone is acetone.

18. A process according to claim 1 where the acid for hydrolyzing the 20-unsaturated steroid (IX) is p-TSA, hydrochloric acid, sulfuric acid, or phosphoric acid.

* * * * *